United States Patent [19]

Delavarenne et al.

[11] 3,953,480
[45] Apr. 27, 1976

[54] EPOXIDATION OF OLEFINS BY HYDROGEN PEROXIDE

[75] Inventors: Serge Delavarenne, Francheville-le-Haut; Francis Weiss, Rethondes; Jean-Pierre Schirmann, Brignais, all of France

[73] Assignee: Produits Chimiques Ugine Kuhlmann, Paris, France

[22] Filed: Sept. 30, 1974

[21] Appl. No.: 510,461

[30] Foreign Application Priority Data
Oct. 2, 1973  France ............................. 73.35113

[52] U.S. Cl. .......................................... 260/348.5 L
[51] Int. Cl.² ........................................ C07D 301/12
[58] Field of Search ............................. 260/348.5 L

[56] References Cited
UNITED STATES PATENTS 3,489,775  1/1970  Seree de Roch et al. ..... 260/348.5 L
3,597,459  8/1971  Mimoun et al. ..................... 260/429
3,654,317  4/1972  Harrod et al. ................. 260/348.5 L
3,778,451  12/1973  Poite ............................ 260/348.5 L

FOREIGN PATENTS OR APPLICATIONS 1,150,060  12/1963  Germany ..................... 260/348.5 V
2,082,811  12/1971  France Primary Examiner—Norma S. Milestone
Attorney, Agent, or Firm—Pennie & Edmonds

[57]  ABSTRACT

An oxirane compound is prepared by reacting an olefinically unsaturated compound with hydrogen peroxide in the presence both of (i) at least one lead compound, exemplarily triethyl lead hydroxide and also of (ii) at least one compound of a group IV-A, V-A or VI-A transition metal exemplarily tungsten hexacarbonyl. The epoxided products are useful in the manufacture of plastics, adhesives and the like.

10 Claims, No Drawings

EPOXIDATION OF OLEFINS BY HYDROGEN PEROXIDE

BACKGROUND OF THE INVENTION

The present invention provides a new method of catalytic epoxidation of ethylenically unsaturated compounds.

The oldest industrial technique epoxidizing double bonds is the procedure via the chlorohydrin which uses chlorine as the oxidizing agent. This method has its disadvantges, in particular the simultaneous production of calcium chloride as a by-product of the dehydrochlorination of the chlorohydrin which has low economic value.

It is also known that ethylene can be epoxidized in good yield in the vapor phase by molecular oxygen over a catalyst based on silver. However such technique is not applicable to olefins in general because it lacks selectivity and give rise to undesired by-products of oxidation.

Other epoxidation methods have been proposed which carry out oxidation by air in two steps. For example, in U.S. Pat. No. 3,351,635 a hydrocarbon such as isobutane or ethylbenzene is oxidized by air to a corresponding hydroperoxide. This intermediate hydroperoxide is then reacted with the olefin in the presence of a compound of vanadium, molybdenum or tungsten. However this method has the disadvantage of producing a low-cost alcohol as a by-product in amount chemically equivalent to the epoxidized compound formed.

It has also been proposed to exploit hydrogen peroxide as an oxidizing agent in the presence of a catalyst such as tungstic acid or in the presence of a nitrile as disclosed in U.S. Pat. No. 3,053,856. These two methods also are not satisfactory, because in the first case the epoxide is not obtained but the corresponding glycol is obtained instead, whereas in the second case there is obtained along with the epoxide an equivalent quantity of the amide corresponding to the starting nitrile. The economic interest for such a method is thus strongly dependent on the value of the by-product.

There has also been described in Belgium Pat. No. 747,316 a method whereby hydrogen peroxide is utilized as epoxidation agent in the presence of a catalyst based on organic derivatives of tin. However, the latter compounds have not been available industrially.

SUMMARY OF THE INVENTION

A new catalytic method has now been found whereby olefins can be epoxidized by hydrogen peroxide in the presence of substances widely available in commerce.

Briefly stated, the instant invention provides a method for preparing an oxirane compound which comprises reacting an olefinically unsaturated compound with hydrogen peroxide in the presence of a catalytic system including both (i) at least one lead compound and also (ii) at least one compound of a second catalytic element which is a transition metal from IV-A, V-A or VI-A in the Periodic Table.

DETAILED DESCRIPTION

The lead compound used in the method of this invention is any compound of lead soluble in the reaction medium which has at least one hydroxyl group or at least one functional group capable of being converted to a hydroxyl or hydroperoxyl group, —OOH, in the presence of aqueous hydrogen peroxide. Thus the lead compound can be a derivative of lead wherein the groups bonded to the lead are bonded by polar or non-polar valence bonds. The lead compound can be added to the reaction medium in an anhydrous or hydrated form. It can be a completely inorganic compound, such as lead sulfate; or a salt having an organic anion, such as lead benzenesulfonate; or an organolead compound such as triethyl lead hydroxide or di(triethyl lead) monohydrogen phosphate.

Thus said lead compounds include lead hydroxide and basic hydroxide $Pb_2O(OH)_2$, and any soluble lead salt. With a few exceptions such as lead tetraacetate, most such salts are salts of divalent lead, being derivable from the neutralization of plumbous hydroxide by inorganic acids or by aliphatic or aromatic carboxylic or sulfonic acids having up to 20 carbon atoms and having anions stable under the conditions of reaction. Thus there can be used lead fluoride, lead chloride, lead bromide, lead iodide, lead nitrate, lead sulfate, lead bisulfate, lead phosphate $Pb_3(PO_4)_2$ lead hydrogen phosphate $PbO_2P(O)OH$, lead dihydrogen phosphate $Pb[OP(O)(OH)_2]_2$, lead pyrophosphate, lead polyphosphates, lead borate, lead carbonate, lead formate, lead acetate, lead propionate lead butyrate, lead isobutyrate, lead hexanoate, lead octanoate, lead dodecanoate, lead napththenate, lead stearate, lead oxalate, lead succinate, lead glutarate, lead adipate, lead benzoate, lead phthalate, lead methane sulfonate, lead ethane sulfonate, lead benzene sulfonate, lead p-toluenesulfonate and the like. These salts can be added as such or they can be formed in situ by adding lead hydroxide and the corresponding acid to the reaction medium.

Organolead compounds used in this invention are compounds of tetravalent lead having from one of three of its four valences bonded to an organic group which is a straight-chained $C_1$–$C_{12}$ alkyl or a $C_3$–$C_{12}$ branched or cyclic alkyl or a $C_3$–$C_{11}$ straight-chained alkylene or a $C_6$–$C_{12}$ aryl, and having the remainder of its four valences bonded to at least one anionic group which is a hydroxyl group or a group which is convertible to a hydroxyl or hydroperoxyl group in the presence of aqueous hydrogen peroxide, said convertible group being a halogen or an anion of a mineral or organic acid, or a $C_1$–$C_{12}$ alkoxy or phenoxy group or an oxide anion formed by the loss of a proton from an organolead hydroxide; wherein said organic groups can be identical to or different from each other and wherein said anionic groups can be identical to or different from each other.

The valence bonds can be non-polar or polar and polyvalent anions can correspond to a plurality of lead atoms. Using ethyl as an example of an organic group the organolead compound can illustratively be triethyl lead hydroxide $(C_2H_5)_3Pb$ OH, triethyl lead chloride $(C_2H_5)_3Pb$ Cl, triethyl lead sulfate $[(C_2H_5)_3Pb]_2SO_4$ or triethyl lead phosphate $[(C_2H_5)_3Pb]_3PO_4$; diethyl lead dihydroxide $(C_2H_5)_2 Pb(OH)_2$, diethyl lead bromide $(C_2H_5)_2 Pb Br_2$, diethyl lead sulfate $(C_2H_5)_2 Pb SO_4$, or diethyl lead phosphate $[(C_2H_5)_2 Pb]_3[PO_4]_2$.

Likewise, using phenyl as an example of an aryl group, the organolead compound can illustratively be triphenyl lead butyrate, diphenyl lead dibutyrate or phenyl lead tributyrate.

Alkyl groups which can be used in the organolead compounds of this invention are exemplarily methyl, ethyl, propyl, isopropyl, n-butyl, sec.-butyl, tert.-butyl, n-amyl, isoamyl, tert.-amyl, n-hexyl, cyclohexyl, the pentyls, n-octyl, capryl, 2-ethylhexyl, nonyls, decyls, undecyls and lauryl.

Alkylene groups which can be used in the organolead compounds of this invention are exemplarily tetramethylene and pentamethylene groups.

Aryl groups which can be used in the organolead compounds of this invention are exemplarily phenyl, o-cresyl, m-cresyl, p-cresyl; p-ethylphenyl, p-isopropylphenyl, p-hexylphenyl and the like.

Anions of acids which can be used in the composition of the organic lead compounds of this invention include exemplarily chloride, bromide, iodide, fluoride, nitrate, bisulfate, sulfate, phosphate, monohydrogen phosphate, dihydrogen phosphate, pyrophosphate, polyphosphates, borate, carbonate, thiophosphate, arsenate, titanate, vanadate, selenate, molybdate, tungstate, formate, acetate, propionate, butyrate, isobutyrate, hexanoate, octanoate, dodecanoate, naphthenate stearate, oxalate, succinate, glutarate, adipate, benzoate, phthalate, acetylacetonate, methanesulfonate, ethanesulfonate, benzenesulfonate, toluenesulfonates and the like.

Examples of alkoxy and phenoxy groups include methoxy, ethoxy, propoxy, butoxy, hexyloxy, octyloxy, lauroxy, phenoxy, cresoxy, p-ethylphenoxy, p(n-propyl)oxy, p-hexylphenyloxy and the like.

Examples of compounds with the anion formed by the loss of a proton from an organolead hydroxide are the trialkyl and triaryl plumboxanes $R_3Pb-O-PbR'_3$ wherein R and R' are any of the above recited alkyl or aryl groups, the same or different. Thus, by way of illustration, such a compound can be di(triethyl lead) oxide $(C_2H_5)_3$ Pb-O-Pb $(C_2H_5)_3$.

Types of organo lead compounds which are particularly suitable for use in the instant invention are the hydroxides, and salts with the above recited anions, of trialkyl lead, triaryl lead, dialkyl lead and diaryl lead; the methoxides, ethoxides and phenoxides of trialkyl lead and triaryl lead; and the trialkyl and triaryl plumboxanes.

Any of the alkyl, alkylene and aryl groups in the organolead compounds used in this invention can optionally be modified by substitution thereon of functional groups stable in the reaction medium such as by hydroxyl, chlorine, fluorine, bromine, iodine, nitro, nitroso, methoxy, ($C_1$–$C_{12}$) alkoxy, amino, carboxyl, ester, amide, nitrile groups and the like.

The organolead compound can be added to the reaction medium directly as such, or it can be prepared in situ from other lead compounds; for example a salt of triethyl lead can be prepared in the reaction medium by reacting tetraethyl lead with an acid such as sulfuric or phosphoric acid.

The preferred lead compounds to be used in carrying out the method of this invention are triethyl lead hydroxide, triethyl lead dihydrogen phosphate and di(triethyl lead) monohydrogen phosphate. The amount of lead compound used in the reaction is between 0.01% and 10% of the weight of the total reaction mixture with the preferred amount being between 0.1% and 2% of the total reaction mixture.

The second constituent of the catalytic system of this invention (i.e. the compound of said second catalytic element) comprises at least one compound of a transition metal said transition metal being a metal in groups IV-A, V-A or VI-A of the periodic table namely, titanium, zirconium, hafnium, vanadium, niobium, tantalum, chromium, molybdenum or tungsten. The preferred metals are vanadium, molybdenum, tungsten and titanium. Examples of their compounds which are useful in this invention are their naphthenates, acetylacetonates, stearates, octoates and polyacids and, in particular, their carbonyls, also their inorganic oxides, such as vanadium oxide, molybdenum oxide, tungsten oxide and titanium oxide; their oxygen acids as vanadic, molybdic, tungstic and titanic acids and their salts; and the phosphates, nitrates, sulfates, carbonates, arsenates of the metals. The preferred second constituents of the instant catalyst system are tungsten hexacarbonyl and molybdenum hexacarbonyl. The amount of compounds of metals in groups IVA, VA or VIA of the Periodic Table used in the reaction is between 0.01% and 10% of the weight of the total reaction mixture with the preferred amount being between 0.1% and 2% of the total reaction mixture.

The two constituents (i) and (ii) of the catalyst system of this invention can be added as separate substances, but can also be part of the same molecule; for example it is within the scope of this invention to add both catalyst constituents together in the form of triethyl lead tungstate or triphenyl lead molybdate or triethyl lead selenate or to use a complex such as $(R)_3PbW(CO)_5$. Also composite salts can be used derived from exemplarily phosphotungstic acid, phosphomolybdic acid, phosphovanadic acid, phosphoselenic acid and the like, in particular the salts of these acids with lead, trialkyl lead and triaryl lead.

Olefinically unsaturated materials which are epoxidized in accordance with the instant invention include substituted and unsubstituted aliphatic and alicyclic olefins which can be hydrocarbons, esters, alcohols, ketones or ethers or the like. Exemplarily the method can be used to epoxidize ethylene, propylene, the butenes, butadiene, the pentenes, 1-hexene, 3-hexene, 1-heptene, 1-ocetene, 2-octene, diisobutylene, 1-nonene, 1-decene, limonene, pinene, myrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, the polybutadienes, styrene, alpha-methyl styrene, divinyl benzene, indene, stilbene, cyclopentene, cyclohexene, cycloheptene, cyclooctene, cyclooctadiene, cyclododecene, cyclododecatriene, cyclopentadiene, vinylcyclohexene, methyl allyl ketone, allyl chloride, allyl bromide, methacrylic acid, acrylic acid, crotonic acid, vinylacetic acid, crotyl chloride, methallyl chloride, the dichlorobutenes, allyl alcohol, allyl carbonate, allyl acetate, alkyl methacrylates, alkyl acrylates, diallyl maleate, dialkyl phthalate, the unsaturated glycerides such as soybean oil, sunflower or turnsole oil, corn oil, cottonseed oil, olive oil, castor oil, peanut oil, talloil, tallow, linseed oil, unsaturated fatty acids such as oleic acid, linolenic acid, erucic acid, the eleostearic acids, elardic, myristoleic, palmitoleic, licanic, lauroleic, ricinoleic and arachidonic acids and the like, and their esters.

In general, olefins which are epoxidizable by the instant invention include substances having the formule

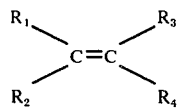

wherein $R_1$, $R_2$, $R_3$ and $R_4$ are identical or different and are hydrogen, a linear $C_1$–$C_{30}$ alkyl, a $C_3$–$C_{12}$ branched or cyclic alkyl, a $C_6$–$C_{12}$ hydrocarbon radical containing a benzene ring, or where $R_1$ and $R_2$ together, or $R_3$ and $R_4$ together, represent a linear or branched $C_3$–$C_{11}$ alkylene radical; $R_1$, $R_2$, $R_3$ and $R_4$ being optionally unsaturated and/or substituted by functional groups stable to the reaction medium, said functional groups being hydroxyl, chlorine, fluorine, bromine, iodine, nitro, nitroso, methoxy, $C_1$–$C_{12}$ alkoxy, amino, carbonyl, ester, amide or nitrile.

A preferred procedure for epoxidizing ethylenically unsaturated compounds according to the method of this invention comprises causing the olefin and hydrogen peroxide to react in the presence of the two-component catalyst and in the presence of a solvent facilitating the homogenization of the mixture. The solvent is preferably a lower alkanol, exemplarily methanol, ethanol, n-propanol, isopropanol, n-butanol, isobutanol, secondary butanol and tertiary butanol, a nitrile such as acetonitrile, or an amide such as dimethylformamide, or an ether, exemplarily dioxane and tetrahydrofurane.

The reaction can be carried out at atmospheric pressure or at a higher pressure to about 100 atmospheres, as when it is necessary thus to maintain the olefin dissolved in the reaction medium. A pressure between about 1 and 50 atmospheres is particularly suitable. The temperature of reaction is suitably between about 0° and 100°C. A temperature between 50°C and 100°C is particularly suitable. The pH of the medium is suitably between about 6 and 9, preferably about 7–8. To adjust the pH in these ranges it is convenient to use a hydroxide or carbonate of an alkali metal or alkaline-earth metal, or as the case may be, an acid selected suitably from the commonly available acids such as hydrochloric, sulfuric or phosphoric acids and the carboxylic and sulfonic aliphatic and aromatic acids having up to about 20 carbon atoms.

The duration of reaction time depends on the nature of the olefin being epoxidized and upon the nature and concentrations of the catalytic constituents. The time of reaction can vary from several minutes to 100 hours or more.

The reactants can be contacted in equimolecular quantities, but it is possible also to use an excess of olefin or of hydrogen peroxide. A suitable range is 0.1 to 5 moles olefin per mole of hydrogen peroxide, but it is preferred to use from about 1 to 2 moles of olefin per mole of $H_2O_2$. The hydrogen peroxide can be used in its usual commercial form as an aqueous solution having a weight concentration of about 30 to 90 %.

The reactants can be introduced into the reaction solution simultaneously or either reactant can be added gradually to the other at a rate and temperature achieving suitable control of the exothermic heat of reaction.

It is advantageous to add to the reaction medium an agent for stabilizing the hydrogen peroxide such as exemplarily phosphoric acid, nitrilotriacetic acid, ethylene diaminotetracetic acid or their sodium salts.

The oxirane compounds which can be prepared by the method of this invention have many uses. In particular, epoxidized substances are utilized in the manufacture of polymers and plastics, adhesives, plasticizing agents and related products.

The invention will be further illustrated by description in connection with the following specific examples of the practice of it wherein, as also elsewhere herein, proportions are in parts by weight unless stated otherwise.

In these examples, the amount of $H_2O_2$ consumed was determined by titration of the unreacted $H_2O_2$ with standardized thiosulfate solution (about 0.1 normal) using $KI_3$ as indicator. The amount of epoxide formed was determined by gas chromatography. The mole percent epoxide formed per $H_2O_2$ consumed is designated as the "selectivity".

EXAMPLE 1

In a reactor held at 70°C, a mixture is made of 0.186 grams of triethyl lead hydroxide (0.6 millimol), 14 grams of n-propanol, 4.5 grams of cyclohexene (55 millimols), 0.1 gram of tungsten hexacarbonyl, 0.68 grams of phosphoric acid and 1.2 grams of a 70 % by weight aqueous solution of hydrogen peroxide (35.7 millimols). After 2 hours of reaction, analysis by gas chromatography of the reaction mixture shows that 2.6 grams of epoxycyclohexane (26.5 millimols) have been formed and tests show that 92 % of the hydrogen peroxide has been consumed. Thus 81 % of the hydrogen peroxide consumed was effective in epoxidizing the cyclohexene, i.e. the selectivity of the reacted $H_2O_2$ for epoxidizing cyclohexene was 81 %.

EXAMPLE 2

Example 1 is repeated except that the lead derivative is omitted. Only 0.49 grams of epoxycyclohexane (1.98 millimols) are formed and only 27.2 % of the $H_2O_2$ is consumed. Thus only 20 % of the reacted $H_2O_2$ was effective in epoxidizing cyclohexene, i.e. the selectivity was only 20 %. This is not an example of the present invention.

EXAMPLE 3

A mixture at 70°C is made of 5 grams n-propanol, 5.7 grams cyclohexene (63 millimols), 0.3 grams of di(-triethyl lead) monohydrogen phosphate [$(C_2H_5)_3$ Pb]$_2$ $PO_4H$ (0.45 millimols), 100 milligrams of tungsten hexacarbonyl and 1.84 grams of a 70 % solution of $H_2O_2$ in water (38 millimoles). After 2 hours of reaction, gas phase chromatography shows that 2.65 grams of epoxycyclohexane (27 millimoles) are formed and the consumption of $H_2O_2$ is 98 %, corresponding to a selectivity of 73 %.

EXAMPLE 4

Example 3 is repeated except that instead of the di(triethyl lead) phosphate there is used an equal weight of mono(triethyl lead) dihydrogen phosphate $(C_4H_5)_3$ Pb $PO_4$ $H_2$.

After 2 hours of reaction, analysis shows that 2.45 grams of epoxycyclohexane are produced, the conversion of $H_2O_2$ is 94.6 % and the selectivity is 72 %.

EXAMPLE 5

Over a period of 2 hours, the following mixture is heated at 80°C.

14 grams propanol 4.25 grams cyclohexene (52 millimoles)
0.261 grams triethyl lead arsenate (0.6 millimole)
0.100 grams tungsten hexacarbonyl
1.8 grams 70 % (by weight) aqueous solution of hydrogen peroxide (37.5 millimols)

The yield found by gas chromatography is 2.46 grams of epoxycyclohexane (25.2 millimoles) corresponding to a selectivity of 69 % for a hydrogen peroxyde conversion of 97.5 %.

EXAMPLE 6

A mixture is prepared of 5.5 grams cyclohexene, 15 grams propanol, 0.250 grams triethyl lead benzoate, 100 mg tungsten hexacarbonyl and 1.85 grams of 70 % hydrogen peroxide (38 millimoles). After 2 hours of reaction at 70°C, the mixture is found to contain 2.16 grams of epoxycyclohexane (22 millimoles), corresponding to a selectivity of 69 % of the $H_2O_2$ with a conversion of 87 %.

EXAMPLE 7

Example 6 is repeated except that the benzoate is replaced by 0.250 grams of triethyl lead selenate (0.6 millimoles). After 2 hours of reaction, the mixture is found to contain 1 gram of epoxycyclohexane which corresponds to a selectivity of 33 % of the $H_2O_2$ with a conversion of 84.5 %.

EXAMPLE 8

There is reacted at 70°C a mixture of 14 grams propanol, 6.1 grams of cyclohexene (74 millimoles), 0.18 grams lead hydrogen phosphate (0.6 millimole), 100 mg tungsten hexacarbonyl and 1.9 grams of aqueous 70 % by weight solution of hydrogen peroxide (39 millimoles). After two hours, the mixture is found to contain 0.2 grams epoxycyclohexane, corresponding to a selectivity of 5.75 % based on the weight of $H_2O_2$ with conversion of 93 % of the $H_2O_2$.

EXAMPLE 9

In 14 grams n-propanol, there is dissolved 0.194 grams tetraethyl lead (0.6 millimoles) and 0.59 grams of phosphoric acid (0.6 millimoles). There is then added 6 grams cyclohexene (73 millimoles), 100 mg tungsten hexacarbonyl and 1.97 grams of aqueous 70 % by weight hydrogen peroxide solution. After 2 hours reaction at 70°C, the amount of epoxycyclohexane determined by gas chromatography is 1.15 grams (11.8 millimoles) corresponding to a selectivity of 34 % based on $H_2O_2$ converted 93.5 %.

EXAMPLE 10

Example 8 is repeated except that the lead hydrogen phosphate is replaced by the hydrogen tungstate of triethyl lead (0.6 millimole). The epoxycyclohexane found by analysis is 1.75 grams (18 millimoles) corresponding to a selectively of 47.7 % for a $H_2O_2$ conversion of 93 %.

EXAMPLE 11

Example 3 is repeated except that the tungsten hexacarbonyl is replaced by 100 grams of molybdenum hexacarbonyl. After 2 hours of reaction, the epoxycyclohexane found is 0.71 grams (7.2 millimoles) corresponding to a selectivity of 46 % for a $H_2O_2$ conversion 40.8 %.

EXAMPLE 12

A mixture is made of 14 grams n-propanol, 4.9 grams cis-2-heptene (50 millimoles), 0.23 grams monophosphate of triethyl lead, 100 grams of tungsten hexacarbonyl and 2.1 grams of aqueous 70 % solution of hydrogen peroxide (43.5 millimoles). This mixture is maintained at 70°C for 2 hours. Gas chromatography shows that 3.5 grams of epoxide of 2-heptene (31 millimoles) have been produced, corresponding to a selectivity of 74 % for a $H_2O_2$ conversion of 97 %.

EXAMPLE 13

Example 12 is repeated except that the cis-2-heptene is replaced by 5.2 grams of cycloheptene (54 millimoles). The amount of epoxycycloheptane found after 2 hours of reaction is 4.15 grams (37.1 millimoles) corresponding to a selectivity of 85 % for a $H_2O_2$ conversion of 97 %.

EXAMPLE 14

Over a period of 2 hours a mixture is heated at 70°C prepared from 15 grams n-propanol, 5.7 grams styrene (58 millimoles), 0.23 grams of triethyl lead phosphate (0.6 millimole), 100 mg of tungsten hexacarbonyl and 1.7 grams of an aqueous 70 % solution of hydrogen peroxide (37.3 millimoles). Gas chromatography shows that 1.6 grams (14 millimoles) of the epoxide of styrene have been formed corresponding to a selectivity of 52 % for a $H_2O_2$ conversion of 76 %.

EXAMPLE 15

Example 14 is repeated except that the styrene is replaced by 11.5 grams octadecene (46 millimoles). After 2 hours of reaction, 0.7 grams of octadecene epoxide is produced. This corresponds to a selectivity of 8 % for a $H_2O_2$ conversion of 75 %.

EXAMPLE 16

A mixture is prepared of 11 grams tertiary butyl alcohol, 4.1 grams cyclohexene (50 millimoles), 0.23 grams of the monophosphate of triethyl lead (0.6 millimoles), 100 mg of tungsten hexacarbonyl and 1.45 grams of an aqueous 70 % solution of hydrogen peroxide. This mixture is kept at 70°C for 10 hours. Gas chromatography shows that 1.55 grams of epoxycyclohexane are produced, corresponding to a selectivity of 58 % for a $H_2O_2$ conversion of 93 %.

EXAMPLE 17

Into a 1-liter autoclave, there is introduced 250 grams of n-propanol, 1.15 grams of triethyl lead phosphate (3 millimoles) and 500 milligrams of tungsten hexacarbonyl. The mixture is heated to 70°C, then propylene is passed in under a pressure of 3 atmospheres. When the solution is saturated, 4.8 grams of aqueous 70 % hydrogen peroxide solution (0.1 mole) is introduced with the aid of a metering pump. After 2 hours and 30 minutes of reaction, gas chromatography shows the formation of propylene oxide with 6 % selectivity for 52 % conversion of $H_2O_2$.

EXAMPLE 18

A mixture is prepared of 20.5 grams cyclohexene (250 millimols), 61 grams N,N-dimethylacetamide, 1 gram di-(triethyl lead) monohydrogen phosphate, 500 milligrams tungsten hexacarbonyl and 8 grams of a 70% solution of $H_2O_2$ in water (164 millimols). After 4 hours of reaction at 70° C the mixture is found to contain 10.9 grams of epoxycyclohexane (111 millimols) corresponding to a selectivity of 70% with a $H_2O_2$ conversion of 96%.

EXAMPLE 19

There is reacted at 70° C a mixture of 35 grams 1,4-dioxane, 41 grams of cyclohexene (500 millimols), 0.8 gram di-(triethyllead) monohydrogen phosphate, 400 milligrams tungsten hexacarbonyl and 5.8 grams of a 70% solution of $H_2O_2$ in water (121 millimols). After 1 hour reaction, the amount of epoxycyclohexane determined by gas chromatography is 6.5 grams (66 millimols) corresponding to a selectivity of 67% with a $H_2O_2$ conversion of 80%.

EXAMPLE 20

A mixture is made of 15 grams acetonitrile, 4.1 grams cyclohexene (50 millimols), 0.5 gram mono-(triethyl lead) dihydrogen phosphate, 100 milligrams tungsten hexacarbonyl and 1.6 gram of a 70% solution of $H_2O_2$ in water (32 millimols). After 6 hours of reaction at 70° C analysis by gas chromatography shows that 2.94 grams (30 millimols) of epoxycyclohexane have been formed corresponding to a selectivity of 100% with a $h_2O_2$ conversion of 94%.

We claim:

1. A method for preparing an oxirane compound which comprises reacting an olefin with hydrogen peroxide in a solvent selected from a lower alkanol, a nitrile, an amide, and an ether, in the presence of a catalyst system including:
   a. molybdenum hexacarbonyl or tungsten hexacarbonyl, or a mixture thereof; and
   b. an organolead compound of tetravalent lead having from one to three of its four valences bonded to an organic group which is a straight-chained $C_1$–$C_{12}$ alkyl radical, a $C_3$–$C_{12}$ branched or cyclic alkyl radical, a $C_3$–$C_{11}$ straight-chained alkylene radical, or a $C_6$–$C_{12}$ aryl radical, and having the remainder of its four valences bonded to at least one anionic group which is a hydroxyl group or a group which is convertible to a hydroxyl or hydroperoxyl group in the presence of aqueous hydrogen peroxide, said convertible group being a halogen or an anion of a mineral or organic acid, or a $C_1$–$C_{12}$ alkoxy or phenoxy group or an oxide anion formed by the loss of a proton from an organolead hydroxide, wherein said organic groups can be identical to or different from each other and wherein said anionic groups can be identical to or different from each other.

2. The method of claim 1 wherein the organolead compound is triethyl lead dihydrogen phosphate.

3. The method of claim 1 wherein the catalyst system is a mixture of triethyl lead dihydrogen phosphate and tungsten hexacarbonyl.

4. The method of claim 1 wherein the reaction takes place at between about 0° and 100°C and at between about 1 and 100 atmospheres and wherein each of
   a. molybdenum hexacarbonyl or the tungsten hexacarbonyl, or the mixture thereof, and
   b. the organolead compound
comprises about 0.01 to 10% based on the weight of the total reaction mixture.

5. The method of claim 1 wherein at least one of the organic groups bonded to the lead is substituted by a halogen atom or a hydroxy, nitro, nitroso, methoxy, $C_1$–$C_{12}$ alkoxy, amino, carboxyl, ester, amide, or nitrile group.

6. A method for epoxidizing cyclohexene which comprises reacting cyclohexene with hydrogen peroxide in a solvent selected from a lower alkanol, a nitrile, an amide, and an ether, in the presence of a catalyst system including:
   a. molybdenum hexacarbonyl or tungsten hexacarbonyl, or a mixture thereof; and
   b. an organolead compound of tetravalent lead having from one to three of its four valences bonded to an organic group which is a straight-chained $C_1$–$C_{12}$ alkyl radical, a $C_3$–$C_{12}$ branched or cyclic alkyl radical, a $C_3$–$C_{11}$ straight-chained alkylene radical, or a $C_6$–$C_{12}$ aryl radical, and having the remainder of its four valences bonded to at lest one anionic group which is a hydroxyl group or a group which is convertible to a hydroxyl or hydroperoxyl group in the presence of aqueous hydrogen peroxide, said convertible group being a halogen or an anion of a mineral or organic acid, or a $C_1$–$C_{12}$ alkoxy or phenoxy group or an oxide anion formed by the loss of a proton from an organolead hydroxide, wherein said organic groups can be identical to or different from each other and wherein said anionic groups can be identical to or different from each other.

7. The method of claim 6 wherein the organolead compound is triethyl lead dihydrogen phosphate.

8. The method of claim 6 wherein the catalyst system is a mixture of triethyl lead dihydrogen phosphate and tungsten hexacarbonyl.

9. The method of claim 6 wherein the reaction takes place at between about 0° and 100°C and at between about 1 and 100 atmospheres and wherein each of
   a. molybdenum hexacarbonyl or the tungsten hexacarbonyl, or the mixture thereof, and
   b. the organolead compound
comprises about 0.01 to 10% based on the weight of the total reaction mixture.

10. The method of claim 6 wherein at least one of the organic groups bonded to the lead is substituted by a halogen atom or a hydroxy, nitro, nitroso, methoxy, $C_1$–$C_{12}$ alkoxy, amino, carboxyl, ester, amide, or nitrile group.

* * * * *

UNITED STATES PATENT AND TRADEMARK OFFICE
CERTIFICATE OF CORRECTION

PATENT NO. : 3,953,480
DATED : April 27, 1976
INVENTOR(S) : Serge Delavarenne et al It is certified that error appears in the above-identified patent and that said Letters Patent are hereby corrected as shown below:

In the Abstract, line 7, "epoxided" should be --epoxidized--.
Col. 1, line 12, "disadvantages" is misspelled.
       line 20, "give" should be --gives--.
       line 30, "in amount" should be --in an amount--.
Col. 2, line 25, after "propionate" a "," should be inserted.
       line 27, "napththenate" should be --naphthenate--.
       line 35, "one of" should be --one to--.
Col. 3, line 34, "organo lead" should be --organolead--.
Col. 5, lines 35 and 36, the portion in bold face print should be in regular print.
Col. 6, line 45, "5 grams" should be --15 grams--.
Col. 7, reprint the entire column since many of the words are obliterated in the left-hand column, after making the following correction, line 8, "peroxyde" should be --peroxide--.
Col. 9, line 26, "h$_2$0$_2$" should be --H$_2$O$_2$--.

Signed and Sealed this

Thirty-first Day of August 1976

[SEAL]

Attest:

RUTH C. MASON
Attesting Officer

C. MARSHALL DANN
Commissioner of Patents and Trademarks